United States Patent [19]
Brenneisen

[11] Patent Number: 5,911,655
[45] Date of Patent: Jun. 15, 1999

[54] DEVICE FOR SUPPORTING A PATIENT FOR STEREOTACTIC ON-TARGET RADIATION TREATMENT

[76] Inventor: Werner Brenneisen, Raschplatz 5, Hannover, Germany, D-30161

[21] Appl. No.: 08/843,026

[22] Filed: Apr. 11, 1997

[30] Foreign Application Priority Data

Apr. 13, 1996 [DE] Germany ............... 196 14 644

[51] Int. Cl.⁶ .................. A47C 20/00; A61B 19/00
[52] U.S. Cl. ................... 5/622; 5/601; 378/68; 600/429; 606/130
[58] Field of Search .................. 5/622, 601, 943; 606/130; 600/429; 378/68, 209

[56] References Cited

U.S. PATENT DOCUMENTS

| | | | |
|---|---|---|---|
| 4,638,798 | 1/1987 | Sheldon et al. | 606/130 |
| 5,483,961 | 1/1996 | Kelly et al. | 600/429 |
| 5,549,616 | 8/1996 | Schulte et al. | 606/130 |
| 5,675,851 | 10/1997 | Feathers | 5/622 |

FOREIGN PATENT DOCUMENTS

4040789A1  6/1992  Germany.

*Primary Examiner*—Alex Grosz
*Attorney, Agent, or Firm*—Collard & Roe, P.C.

[57] ABSTRACT

A device for supporting a patient for stereotactic on-target radiation therapy in the head region of the patient includes a supporting table with a tabletop movable at least in the horizontal plane, and a holding means for arranging a stereotaxis unit fixed on the head of the patient. The holding means is arranged on the tabletop and is associated with the head region of the patient projecting beyond the tabletop. This device provides aiming accuracy also with not highly rigid connections between a stereotaxis unit and the skull of a patient. This device provides a connection means permitting free relative movability at least in the longitudinal direction of the table or the patient, and at least temporarily between the tabletop and the stereotaxis unit.

4 Claims, 2 Drawing Sheets

DEVICE FOR SUPPORTING A PATIENT FOR STEREOTACTIC ON-TARGET RADIATION TREATMENT

BACKGROUND OF THE INVENTION

1. Field of the Invention

The present invention relates to a device for supporting a patient for stereotactic on-target radiation therapy in the head region of the patient, comprising a supporting table with a tabletop movable at least in the horizontal plane, and a holding means arranged on the tabletop for arranging thereon a stereoaxis unit fixed onto the head of the patient, such holding means being associated with the head region of the patient projecting beyond the tabletop.

2. The Prior Art

When a stereotactic on-target radiation therapy has to be carried out on a patient in the head region of such patient, for example for treating brain tumor radiosurgically, a stereotaxis frame is in most cases first mounted on the head of a patient. As a rule, a computer tomography of the skull of the patient is subsequently carried out, with the stereotaxis unit fixed onto the skull. X-ray pictures of the skull of the patient are obtained in this way, with elements of the stereotaxis unit being recognizable on such pictures. It is possible with the help of these pictures to exactly determine the coordinates of the target, for example a brain tumor, to be treated with radiation therapeutically. The coordinates so found are used for focusing the treatment beam onto the target to be radiated.

The radiation treatment system of the prior art includes a device of the type specified above. Thus, there is a supporting table on which the patient is placed for the radiation treatment, whereby the patient still carries without change the stereotaxis unit; and a holding means on which this stereotaxis unit can be arranged.

The tabletop is movable at least in the horizontal plane, thus, for example, in the longitudinal direction (Z-direction) of the table, and in the transverse direction (orthogonal X-direction) of the table, so that the patient supported on the tabletop is movable in these directions as well. With the help of such movability and by reference to the stereotaxis unit fixed onto the patient, or its coordinates, it is possible to aim the radiation treatment system. This is accomplished by moving the target area within the head of the patient into the so-called iso-center of the radiation treatment system, i.e., into the center in which the radiation axis of the treatment beam and the various axes of rotation of the treatment system meet. Following this alignment of the target, a treatment can be carried out safely onto the target area of the head.

However, a problem exists in these prior art systems in that after the patient has been placed on the supporting table, the stereotaxis unit carried by the patient has to be arranged on the top of the table with the help of the holding means. Normally this requires minor movements of the stereotaxis unit until this unit fits into the holding means at the intended location because it is, of course, not possible to place the patient on the tabletop with corresponding accuracy. These adjusting and attaching movements required for securing the stereotaxis unit onto the holding means, however, are not followed by similar movements of the entire body of the patient. This is because the body of the patient, due to its mass and the frictional forces acting between the body and the tabletop, is immovable by the forces required for securing the stereotaxis unit. Instead, reactive forces build up on the body of the patient, for example due to deformation of soft body parts, which reactive forces correspond with the securing forces but are directed against the securing forces.

If the stereotaxis unit is very rigidly secured onto the head of the patient, which is sometimes done with spikes that drill themselves into bone parts of the skull of the patient, such developing reactive forces are relatively harmless because they are not capable of changing this rigid connection.

However, a less rigid connection between the stereotaxis unit and the head of the patient is sometimes selected. For example, this may result by using a thermoplastic material, which is molded onto the head of the patient like a mask, or by securing the stereotaxis unit by means of a bite block corresponding with a dental impression of the patient. In case of such less tight connection between the head of the patient and the stereotaxis unit, the reactive forces built up are then quite capable of displacing the stereotaxis unit relative to the head of the patient. This displacement can then later lead to inaccuracy in the aiming during the radiation treatment.

SUMMARY OF THE INVENTION

It is an object of the present invention to assure in connection with a stereotaxis device that there be accuracy in the aiming of the device when the connections between a stereotaxis unit and the skull of a patient are not very rigid.

This object is achieved according to the present invention by providing a device for supporting a patient for stereotactic on-target radiation therapy in a head region of the patient, comprising a supporting table with a tabletop movable at least in a horizontal plane; a holding means located on the tabletop for arranging thereon, a stereotaxis unit fixed onto the head of the patient, said holding means being associated with the head region of the patient projecting beyond the tabletop; a connection means permitting free relative movability at least in a longitudinal direction of the supporting table or patient, and at least temporary movability between the tabletop and the stereotaxis unit.

In one embodiment, such connection can be made between the holding means and the stereotaxis unit; in another embodiment such connection can be between the tabletop and the holding means.

With the help of the device according to the invention, it is advantageously possible, for example, to place a patient carrying a stereotaxis unit onto the supporting table of the device according to the invention. Then subsequently the stereotaxis unit carried by the patient is fixed and attached in the usual manner onto the tabletop of the supporting table via the holding means. This attachment, as mentioned above, may first lead to a build-up of reactive forces. Such reactive forces, however, could then be quickly eliminated by permitting free movability of the stereotaxis unit relative to the tabletop within the range of the connection means. It is also possible first to separate i.e. the above-mentioned bite block from the stereotaxis unit before putting the patient on the table. Then it will be possible to dock the bite block carried by the patient with the stereotaxis unit by moving the stereotaxis unit towards the bite block.

Reactive forces can be eliminated in this way either by keeping the tabletop immovable and by letting the stereotaxis unit move relative to the tabletop via the freely movable connection means. This is because the freely movable connection means simply yields to the reactive forces built up. Or, in a second embodiment, such reactive forces could be eliminated by keeping the stereotaxis unit fixed, followed by releasing the entire tabletop with the body of the patient placed thereon with respect to a relative motion, which can be carried out with the help of the connection means.

As soon as the reactive forces have been eliminated, a rigid connection can be made between the stereotaxis unit and the tabletop by adjusting and fixing the connection means. Thus, an exact on-target positioning of the entire patient is subsequently possible by moving the tabletop. The on-target position, once set, will then be retained free of tension.

So that no new forces or tensions can build up during positioning, particularly during fine tuning the positioning of the patient provision is made according to a further embodiment of the device of the invention. Thus, a means for fine tuning the positioning of the patient is associated with the range of the tabletop for jointly moving the tabletop, the holding means and the stereotaxis unit. Thus, the entire patient is moved in this way at least in the longitudinal direction, which is possible relatively free of tension.

With conventional prior art stereotaxis units, a fine positioning means is basically associated only with the head region of the patient, so that fine tuning the positioning may again lead to unfavorable tensions and forces between the head and the body of the patient.

With free movability, the stereotaxis unit preferably should be freely movable in a horizontal plane, thus in two directions orthogonal relative to each other, namely longitudinally and transversely relative to the tabletop or body of the patient. This could be accomplished, for example, by means of two independent guides, for example dovetail guides, which are arranged perpendicularly relative to each other. These guides can be released or locked into position independently of one another, whereby any frictional forces could be minimized by antifriction bearings or the like. However, provision could be made also, for example, by using ball bearing support having negligible frictional forces, because these ball bearings are a priori freely movable in the entire plane. Corresponding mechanical measures are sufficiently known from other areas of application.

BRIEF DESCRIPTION OF THE DRAWINGS

Other objects and features of the present invention will become apparent from the following detailed description considered in connection with the accompanying drawing which discloses two embodiments of the present invention. It should be understood, however, that the drawing is designed for the purpose of illustration only and not as a definition of the limits of the invention.

In the drawing, wherein similar reference characters denote similar elements throughout the several views.

DETAILED DESCRIPTION OF PREFERRED EMBODIMENTS

Figure 1:
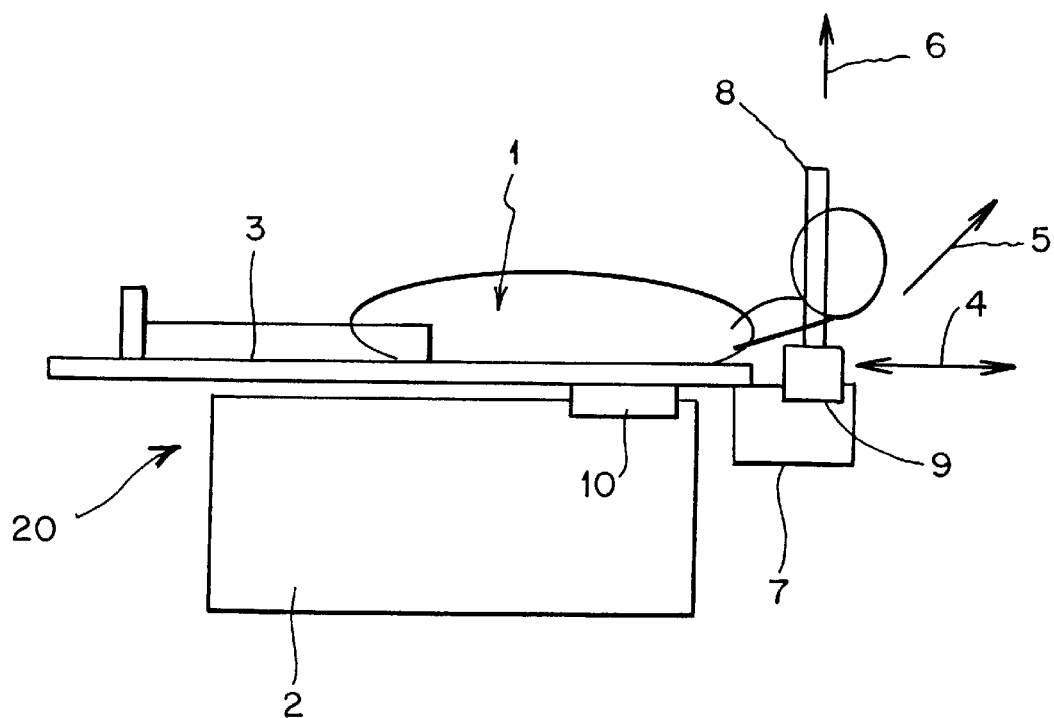
FIG. 1 shows a schematic lateral view of a device according to the invention indicated by block elements, with a patient being located onto the device.
Figure 2:
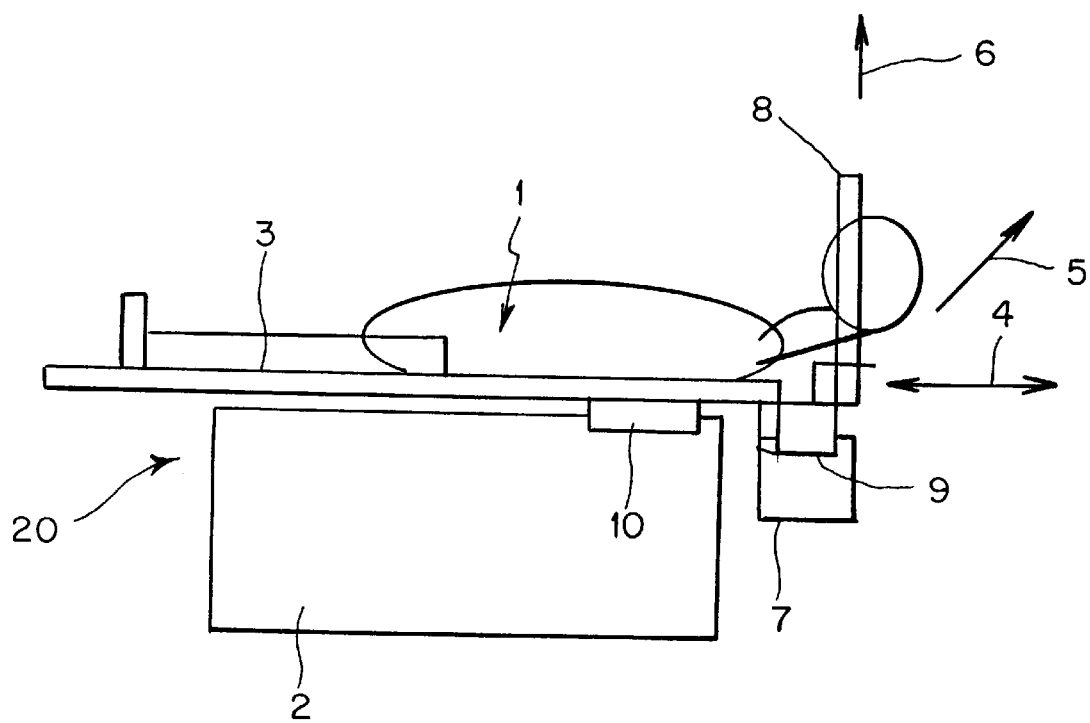
FIG. 2 shows a second embodiment of the invention device.

Turning now in detail to the drawings, the device of the invention shown in FIGS. 1 and 2 and comprises a supporting table 20 for the patient 1. The supporting table 20 includes a table base 2 and a tabletop 3. The tabletop 3 is movable at least in the horizontal plane, but preferably also in the vertical direction. Three coordinate axes may be associated with the three possible directions of movement, namely a Z-axis in the longitudinal direction of the table or patient 1, which is indicated by the double arrow 4. There is an X-axis in the horizontal plane or transversely to Z-axis according to arrow 5; and a Y-axis in the vertical direction according to arrow 6.

A holding means 7 is arranged on the tabletop 3, and a stereotaxis unit 8 is carried by the patient 1 which can be secured onto the holding means 7. In the exemplified embodiment shown in FIG. 1 of the drawing, a connection means 9 is located between the stereotaxis unit 8 and the holding means 7. This connection means 9 is capable of allowing and also blocking free movability of the stereotaxis unit 8 relative to the tabletop 3.

In FIG. 2, a corresponding connection means 9 is shown to be located between the holding means 7 and the tabletop 3. Furthermore, the holding means 7 contains a fine tuning adjustment means with the possibility for finely adjusting the stereotaxis unit 8 in the X- and Y-directions, thus in the directions of arrows 5 and 6.

The means 10 for the fine tuning and adjustment of patient 1 or stereotaxis unit 8 in the Z-direction, thus in the direction of arrow 4, is located on the underside adjacent to the tabletop 3 and connects the table base 2 with the tabletop 3. With this fine adjustment means 10, the entire patient is advantageously displaced in the Z-direction, so that no undesirable forces can build up in this process in the patient himself.

While several embodiments of the present invention have been shown and described, it is to be understood that many changes and modifications may be made thereunto without departing from the spirit and scope of the invention as defined in the appended claims.

What is claimed is:

1. Device for supporting a patient for stereotactic on-target radiation therapy in a head region of the patient, comprising a supporting table (20) with a tabletop (3) movable at least in a horizontal plane;

a holding means (7) located on the tabletop (3) for arranging thereon a stereotaxis unit (8) fixed onto the head of the patient (1), said holding means being associated with the head region of the patient projecting beyond the tabletop;

a connection means (9) permitting free relative movability at least in a longitudinal direction of the supporting table or patient, and at least temporary movability between the tabletop and the stereotaxis unit.

2. Device according to claim 1, wherein the connection means (9) is located between the stereotaxis unit (8) and the holding means (7).

3. Device according to claim 1, wherein the connection means (9) is located between the holding means (7) and the tabletop (3).

4. Device according to claim 1, further comprising a means (10) for fine tuning a positioning of the patient being located adjacent to the tabletop (3) for jointly moving the tabletop (3) with the holding means (7) and the stereotaxis unit (8).

* * * * *